United States Patent [19]
Billet et al.

[11] Patent Number: 5,871,359
[45] Date of Patent: Feb. 16, 1999

[54] CROWN-AND-ROOT RECONSTRUCTION ASSEMBLY MADE OF A COMPOSITE MATERIAL WITH A MODULUS OF ELASTICITY VARYING ALONG A GRADIENT AND METHOD FOR MAKING SAME

[76] Inventors: Gilles Billet, 32, Avenue d'Haussez, F 38500 Voiron; Bruno Clunet-Coste, F 38500 Tolvon; Bernard Duret, Les Travers, F-38470 Saint-Gervais; Christian Fenon, Rue de la Poste, F-69380 Les Cheres; Bernard Maneue, Hameau de la Vouise, F-38500 Voiron, all of France

[21] Appl. No.: 836,303
[22] PCT Filed: Nov. 21, 1995
[86] PCT No.: PCT/FR95/01533
  § 371 Date: May 9, 1997
  § 102(e) Date: May 9, 1997
[87] PCT Pub. No.: WO96/15731
  PCT Pub. Date: May 30, 1996

[30] Foreign Application Priority Data

Nov. 21, 1994 [FR] France .................................. 94/14183

[51] Int. Cl.⁶ ....................................................... A61C 5/08
[52] U.S. Cl. .............................................................. 433/220
[58] Field of Search .................................. 433/220, 221, 433/225

[56] References Cited

U.S. PATENT DOCUMENTS 4,253,829  3/1981  Adelberger ................................. 433/40
5,074,792  12/1991  Bernadat .................................. 433/220
5,328,372  7/1994  Reynaud et al. ......................... 433/220
5,518,399  5/1996  Sicurelli, Jr. et al. ................... 433/220
5,564,929  10/1996  Alpert ..................................... 433/220

FOREIGN PATENT DOCUMENTS

| A 0 432 001 | 6/1991 | European Pat. Off. . |
| A-2 588 181 | 4/1987 | France . |
| 3825601 | 3/1989 | Germany ............................... 433/220 |
| Aa-38 25 601 | 3/1989 | Germany . |
| A-562 605 | 6/1975 | Switzerland . |
| WO 95/08300 | 3/1995 | WIPO . |

*Primary Examiner*—Cary E. O'Connor
*Attorney, Agent, or Firm*—Oliff & Berridge PLC

[57] ABSTRACT

A crown-and-root reconstruction assembly made of a composite materials with a modulus of elasticity varying along a gradient. The assembly comprises a physiological securing post (4) and a crown reconstruction base (1) made of partially or completely light-conducting material. The connection between the crown reconstruction base (1) and the post (4) is achieved by polymerising the material of the base under an isostatic charge. The forming process may be completed by manipulating the material with the fingers through a forming membrane (22) to prevent any gap developing at the interface (10) between the root (8) and the crown reconstruction base (1). A helical arrangement of the fibers (5) of the post (4) ensures that the modulus of elasticity is close to that of the natural dentine, regardless of the angle of incidence at the reconstruction is stressed.

12 Claims, 3 Drawing Sheets

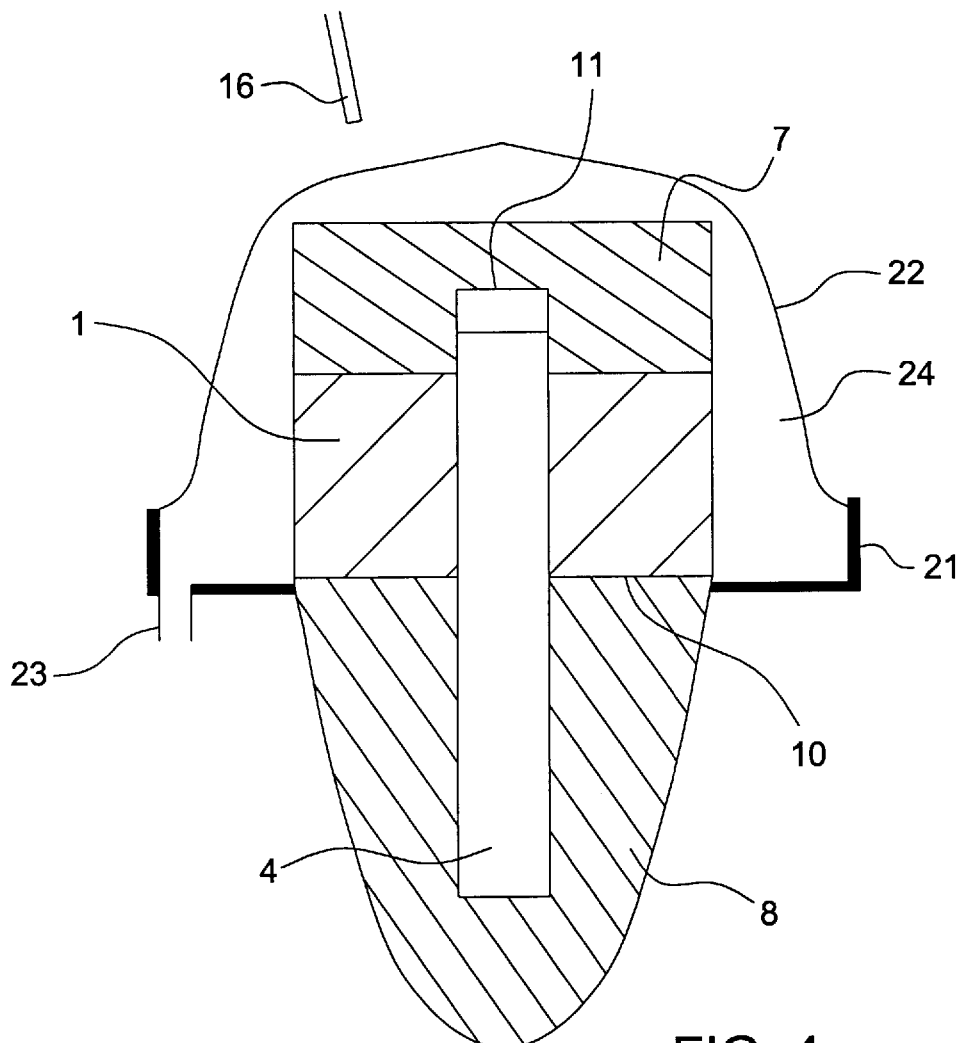
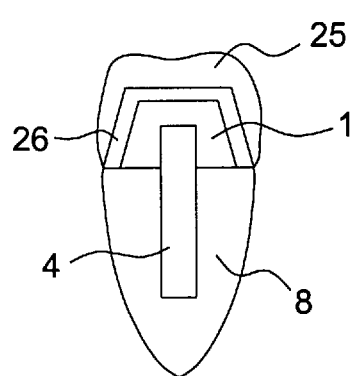

CROWN-AND-ROOT RECONSTRUCTION ASSEMBLY MADE OF A COMPOSITE MATERIAL WITH A MODULUS OF ELASTICITY VARYING ALONG A GRADIENT AND METHOD FOR MAKING SAME

PRIOR ART

This invention deals with a crown-and-root reconstruction assembly for a dental prosthesis, comprised of a physiological securing post and a crown reconstruction base made of composite material tightly connected to the post and applied without any gap to the tooth or to a laboratory model reproduction of the healthy remaining portion of the tooth.

In dentistry, crown-and-root reconstructions generally use posts made out of various metallic alloys that are either prefabricated or cast via indirect technique. The use of metallic posts presents many disadvantages resulting from electro-chemical corrosion and oxidation phenomena or from the clustering of metallic ions in the body. When the crown reconstruction base is cast simultaneously with the post, the crown-and-root reconstruction assembly is homogeneous but its mechanical behavior is far from that of a natural tooth, a fact which results in root fractures in reconstructed teeth.

Posts made out of composite material are also available, in particular those made from high solidity fibers that may possibly be included in organic matrices as composite materials. Such posts are described in documents FR-A-2588181 and EP-A-432001. The reconstruction base is made directly inside the mouth on the natural tooth, with a charged resin or ionomer glass. A carbon fiber and epoxy resin post has a modulus of elasticity (110 GPA) that is identical to that of titanium when it is stressed along the axis of the fibers. The posts can be fabricated by machining cylindrical bars, or they can be made from axial carbon fibers assembled in an organic matrix.

The method consists of lining what remains of the tooth to be reconstructed and inserting the reconstruction product in a pasty state using a spatula or with the fingers. The reconstruction product is composed of two pastes to be mixed at the time of use, and one of the two pastes includes the catalyst. However, in mixing the two pastes, there is the risk of air bubbles becoming incorporated in the mixture, which results in inhibiting the polymerization around each bubble, thus creating areas in which there remain free monomers that are toxic to dental tissues. These poorly polymerized areas are the source of a significant reduction in the reconstruction's mechanical qualities and, are choice areas for discolorations and bacterial growth; they are also a source of cracks and fractures. The double mixture does not allow for the strict control of the components proportions which would ensure complete polymerization.

It is also difficult to use photo-polymerizable reconstruction paste inside the mouth because the product used is very thick. Indeed, the degree of polymerization of a resin is inversely proportionate to the square of the distance to the light source.

When the reconstruction material is manually inserted, the reconstruction paste must have characteristics that allow for easy handling. The resin must be charged with particles or ultra short fibers so that the material retains some viscosity and pegosity in order to ensure easy manual handling. The mechanical characteristics of such a material are weak, with the modulus of elasticity usually in the 4 to 12 Gpa range and tensile resistance does not exceed 60 to 70 Mpa.

Inventors have determined that in a crown-and-root reconstruction assembly, the root dentine, the favored locus for fractures, must be stressed as little as possible. The post must be in a passive state and its role is to maintain the crown portion of the reconstruction base. In the case of a metallic post, in particular, a titanium post, or of a post made of carbon-epoxy fibers, the application of evenly spread pressure on the occlusal face of a root reconstruction causes deformation of the base of the charged resin root reconstruction with a low modulus of elasticity (4 to 12 Gpa). The post will very quickly have to support the entire load, with the risk that it may cause the root to explode in the event of significant pressure on the tooth, particularly. when the force is applied along the axis of the fibers that coincides with the axis of the post and the tooth.

The method of inserting resins charged with particles inside the mouth, a task performed with a spatula or with the fingers and done directly on the post that has been previously sealed into the root, may result in separations between the dentine and the reconstruction base interface. This gap is due to the inevitable contractions that occur during polymerization of organic matrices, and it will be the infiltration point which will threaten the crown-and-root reconstruction's longevity.

OBJECT OF THE INVENTION

This invention seeks to remedy these disadvantages and involves making a crown-and-root reconstruction assembly with great solidity, independently from the angle of incidence of the force applied to the tooth.

The crown-and-root reconstruction assembly pursuant to the invention is characterized by the fact that:

the connection between the crown reconstruction base and the post is achieved by polymerization of the material of said base under an isostatic charge, after placing an auxiliary forming part in the upper part of the base, and the majority of the fibers that reinforce the post are more than 3 mm long and run in a different direction from that of the longitudinal axis of the post, so as to adjust the post's modulus of elasticity close to that of the natural dentine, independently from the angle of incidence of the force applied to the tooth, with an assembly tensile strength greater than 200 MPa.

The presence of long fibers in the composite material of the crown-and-root assembly produces a modulus of elasticity in the 15 to 50 GPa range.

Obtaining a constant and uniform resin/support ratio is the result of an isostatic pressure on the reconstruction base. This leads to a pressing effect which brings the different fibers closer together and releases a certain amount of resin in order to reach the resin/support ratio calculated so as to obtain the modulus of elasticity sought, i.e., 15 to 50 GPa. With the same forming process pressure, the same resin rate is maintained for each reconstruction, along with the same mechanical characteristics.

The identity of the modulus of elasticity of the post and the dentine helps achieve a harmonious flow of mechanical stresses and an absence of stress concentration at the interfaces, in particular at the apical end of the post. Dentine's modulus of elasticity varies from 9 Gpa in the root portion to 20 Gpa in the crown portion. The particular organization of the long fibers that reinforce the post helps adjust the post's modulus of elasticity to that of the tooth dentine from the crown portion of the post (20 Gpa) to the root portion (9 Gpa). In order to avoid the nail effect that might cause the root to explode, the axis of the majority of the post's fibers is along a gradient in relationship to the longitudinal axis of the post, which corresponds to the axis along which masticatory forces are applied.

The consequence is that the root post must also have a modulus of elasticity that is close to that of the crown-and-root dentine, in order to avoid significant changes in the modulus of elasticity which would impede the harmonious flow of stresses across the interfaces.

According to one characteristic of the invention, the fibers of the post are arranged in a helical fashion, either crossed or not crossed, woven or unwoven, where the diameter of the turns and the threading are calculated according to the finite elements method. The long fibers used can be chosen among any high performance fibers, in particular fiberglass E or R, carbon, ceramic, silicon carbide, boron carbide, aramid.

According to another characteristic of the invention, the central core of the post can be made out of a material easily penetrable via mechanical or chemical means and that will serve as a guide for dental instruments during removal of the post, particularly at the time of a subsequent dental work on the root.

The fiber/resin ratio, the diameter, the length and number of fibers from the crown portion to the apical portion of the post are calculated so that the modulus of elasticity of the post will vary from 9 Gpa to 20 Gpa +/−40%, regardless of the angle of incidence of the force that will stress the post.

According to another characteristic of the invention, it uses photo-polymerizable preforms prepared in industrial mode, i.e., that is to say that the photo-polymerizable processes are controlled under laboratory conditions with powerful lighting that guarantees maximum resin conversion rate as well as the homogeneity sought.

DESCRIPTION OF THE DRAWINGS

Other advantages and characteristics will appear more clearly from the following description of an embodiment of the invention given only by way of example, without any limitation thereto. The embodiment is represented in the diagrams appended hereto in which:

FIG. 4 is a view identical to FIG. 1 of an embodiment variation using a vacuum device;

FIG. 5 represents a cross-section of the tooth equipped with a dental prosthesis crowning the crown-and-root assembly according to the invention;

DESCRIPTION OF A PREFERRED EMBODIMENT

Figure 1:
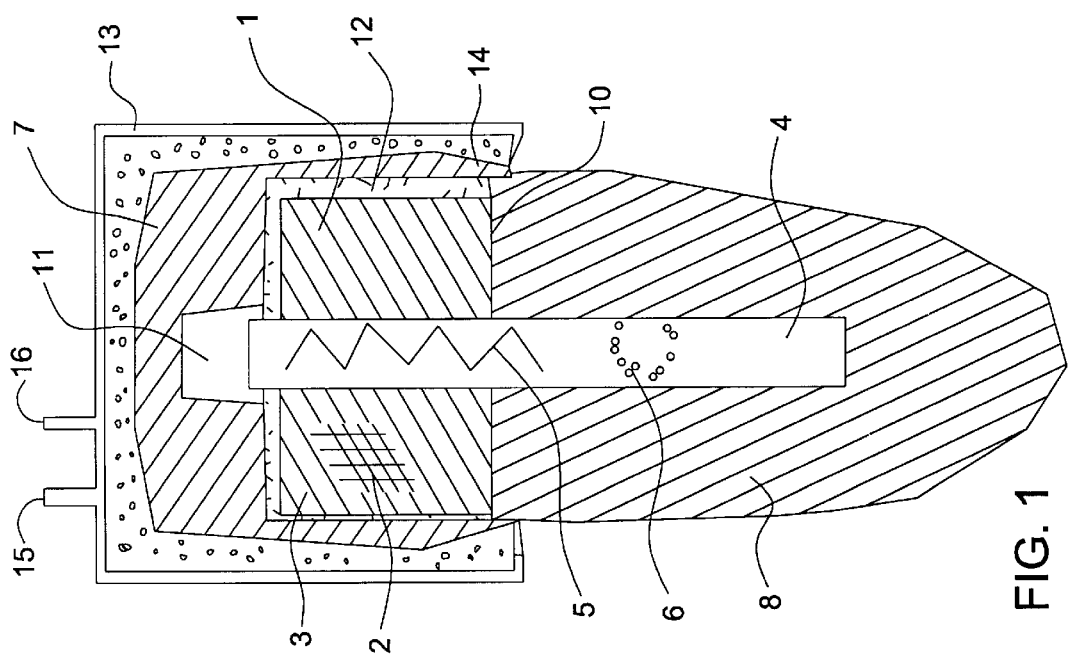
FIG. 1 is a cross-section of a portion of the tooth equipped with a pressure device in order to make the crown-and-root reconstruction assembly according to the invention.

In FIG. 1, the crown-and-root reconstruction assembly features a crown reconstruction base 1, made out of a composite material that includes an initial reinforcement of fibers 2, sunk in an initial matrix 3 and connected to a physiological root post 4. Post 4 is also made out of a composite material equipped with a second reinforcement of fibers 5, sunk into a second matrix 6. Post 4 is lodged axially in a central hole made in the residual root or dentine 8, and the crown reconstruction base 1 rests on the upper face of the root 8.

Figure 2:
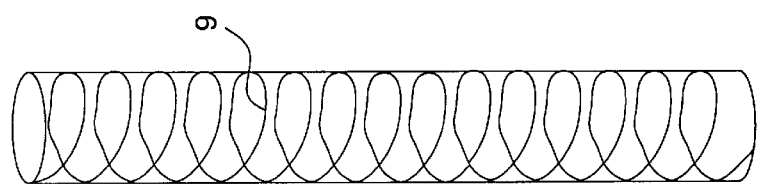
FIG. 2 shows a schematic view of the post represented in FIG. 1 on a larger scale.

According to the invention, the helical structure 9 (FIG. 2) of the second fiber reinforcement 5, associated with a predetermined variation of the diameter of the helicoid, of the threading, of the nature, diameter and rate of fibers, of their crossing or weaving, has made it possible to make post 4 out of a composite material with a modulus of elasticity that is always comparable to that of natural dentine, and that never varies from it by more than 40%, regardless of the angle of incidence of the force stressing post 4. The result is that there are no mechanical stresses at the interfaces of post 4 and dentine 8, in particular at the apical level, and thus there is no mechanical aggression of post 4 on the residual tooth 8. The fibers 5 of the second reinforcement are included in the second organic matrix 6 which can be chosen among any type of organic binding agent, in particular the following resins: epoxy, polyurethane, polyester, acrylic or methacrylic.

The organic matrix 6 of post 4 may also be charged with organic, mineral or metallic particles, designed to change its pegosity, viscosity, surface state and the biocompatibility of post 4. The surface state of the top side of post 4 allows for optimal gluing of post 4 to dentine 8 according to gluing techniques known in the art.

The majority of the reinforcement fibers 5,2 of post 4 and of reconstruction base 1 are never entirely stressed along their large axis. The modulus of elasticity of post 4 is always close to that of dentine 8 and the modulus of elasticity of the reconstruction base 1 is always equal to or greater than that of the crown dentine, independently from the angle of incidence of the force applied to the reconstruction.

An embodiment of the crown reconstruction base has composite material with a quantitative ratio of approximately 75% fibers and 25% resin.

The process of shaping the paste of which reconstruction base 1 is made, is done by applying isostatic pressure exerted after molding a membrane or bladder of a forming device.

An auxiliary intermediate forming part 7 is advantageously applied to the upper surface 12 of the reconstruction paste and can be either circular or ellipsoidal in shape. The material of intermediate part 7 is transparent to light rays, and may be moldable. Forming part 7 is equipped with a dummy positioning hole 11 located straight to post 4 and may be joined to the reconstruction base 1 content.

Forming part 7 is formed according to a piston with a short sliding stroke that also serves as a stop at the upper end of post 4. The paste for reconstruction base 1 comes as a cylindrical or tapered preform which is in a pasty state prior to polymerization (prepegg). It may possibly be included in a case that is part of forming part 7, and is translucent and moldable. It is also possible to incorporate it. inside a syringe or some other opaque container that allows for preservation and application of the paste in order to make the reconstruction.

The preform is positioned on post 4, and is then covered by intermediary part 7. The forming means are then implemented as are the polymerization means. After polymerization, forming part 7 is removed so as to expose the upper face of the reconstruction base 1 and the projecting end of post 4.

In the case of FIG. 1, forming the crown-and-root reconstruction assembly may be achieved inside the patient's mouth. A housing 13 covers the crown-and-root reconstruction assembly and contains an inflatable bladder 14 connected to an appropriate device 15 for injecting fluid at a determined temperature and pressure.

The illumination needed for photo-polymerization is then achieved by way of a light guide that can be made from a fiber optic 16.

In the case of the variation in FIG. 4, extemporaneous forming involves placing a laboratory model of the residual tooth 8 inside an apparatus containing a hermetic enclosure 21 and a translucent elastic membrane 22. A vacuum tube 23 allows for creation of a depression inside the internal space 24, so, as to coat membrane 22 on intermediary shaping part 7, reconstruction paste 1, post 4 and the replica of residual root 8, during the polymerization phase by the rays generated by the fiber optic 16. Forming part 7 is then discarded at the end of the polymerization phase.

This forming method in a vacuum may, of course, be implemented inside the patient's mouth.

The physical behavior of reconstruction base 1 may also be improved by completing the forming process during application of the isostatic pressure, with finger manipulation through membrane 22, thus avoiding any gap at the interface 10 of root 8 and crown reconstruction base 1.

At the end of the polymerization operation, the crown-and-root reconstruction assembly is homogeneous and features a modulus of elasticity that is adapted to the tooth's functional and protective needs, and there is no gap at reconstruction interface 10.

As for FIG. 5, after removal of the auxiliary forming part 7, the reconstruction base 1 is covered by a prosthesis that has a high modulus of elasticity, specifically a metallic or ceramic crown 25, with insertion of a support shell 26 described in document WO 95/08300.

The shell 26 serves as an interface and constitutes a intermediary transitional layer between the rigid crown 25 and the residual tooth 8. This layer is made out of composite material. This shell 26 has a modulus of elasticity close to that of natural dentine and helps dampen shocks.

The prosthesist glues the shell 26 in the laboratory in the lower side of the metallic or ceramic crown 25 and then, in the dentist's office, the dentist performs the process of gluing the crown 25 covered on the reconstruction base 1 with the same type of resin as that used in the formulation of the composite materials for the base 1 and the shell 26.

Figure 3:
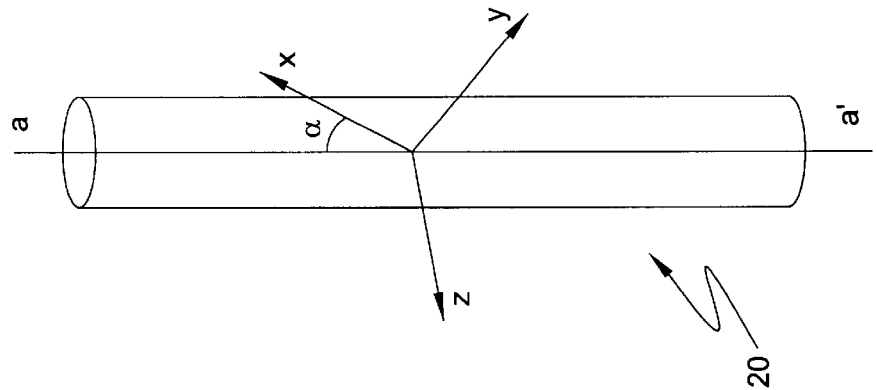
FIG. 3 is a view identical to FIG. 2 of an embodiment variation of the post.

Post 20 according to FIG. 3 is obtained by machining sheets or sections of composite material where the fiber organization is three-dimensional following axes x, y or z. The tooling axis a, a' of post 20 never uses axes x, y or z, and forms an alpha angle of 20° to 70° with axes x, y, z.

Figure 6:
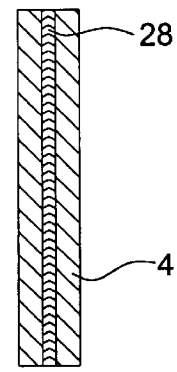
FIG. 6 is a cross-section of another type of post.

As for FIG. 6, the central core of post 4 can be made from a material that is easily penetrable either chemically or mechanically, in order to act as a dental instrument penetration guide, particularly for drills and files, avoiding lateral perforations. The core 28 may be transparent, and in this case serves as a light guide.

Figure 7:
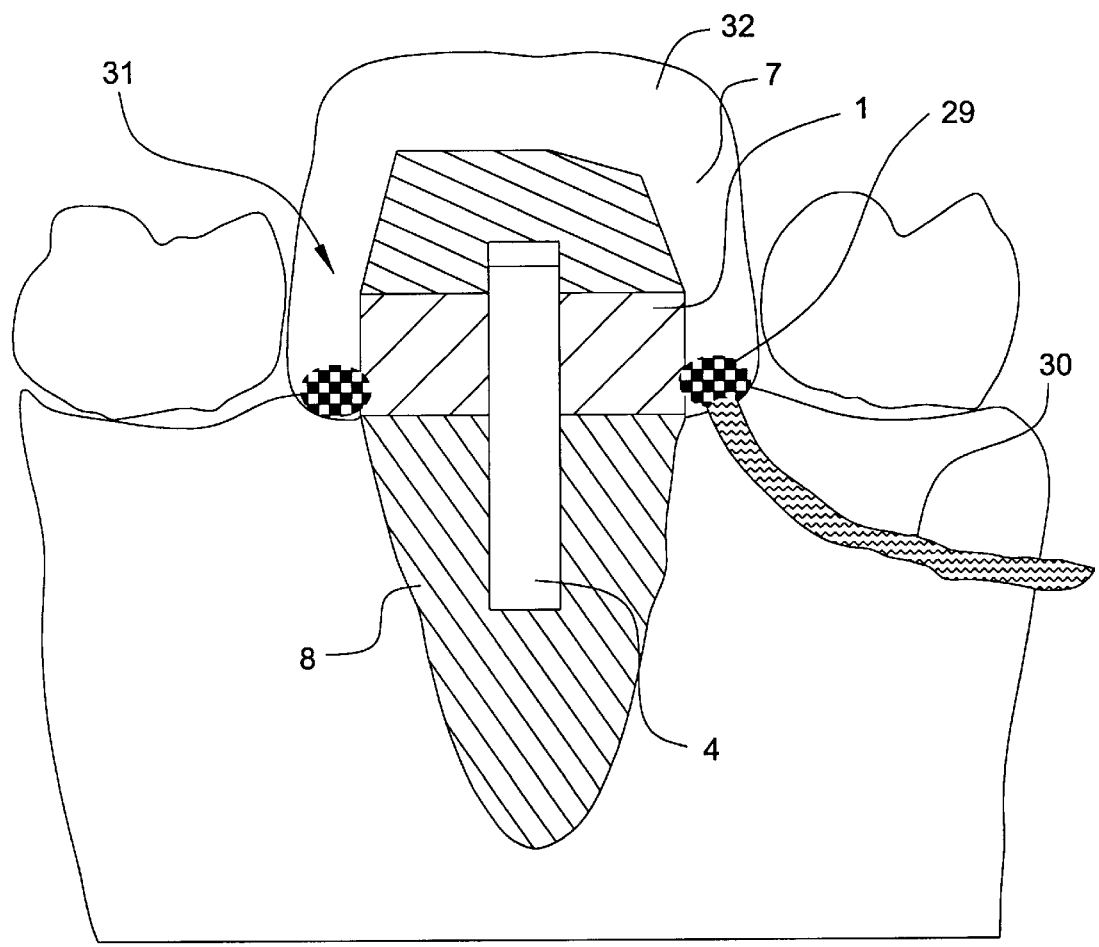
FIG. 7 shows another system for shaping the crown-and-root reconstruction assembly.

FIG. 7 shows a third means for forming the crown-and-root reconstruction assembly. The upper part of the residual root 8 is encircled with a pumping strand 29 connected to a vacuum pump via a connecting tube 30. After the post 4 has been positioned, the reconstruction paste 1 is then applied on the residual root 8 and the forming part 7 is positioned on top of the paste 1.

A watertight mold 31 covers the assembly; it is made from a moldable and transparent material 32, in particular from photo-polymerizable elastomer. The mold 31 ensures peripheral water-tightness, and is molded under vacuum conditions in order to exert the isostatic pressure when the crown reconstruction base 1 undergoes the forming process.

Then, a light source induces photo-polymerization of the reconstruction base 1 through forming part 7 and the material 32 of mold 31, while maintaining the isostatic pressure.

We claim:

1. Crown-and-root reconstruction assembly for a dental prosthesis, including a crown reconstruction base (1) made of a composite material with an initial reinforcement of fibers (2) sunk in an initial matrix (3) and connected to a physiological root post (4) also made from a composite material equipped with a second reinforcement of fibers (5) sunk into a second matrix (6), where said crown reconstruction base (1) rests on the upper face of the root (8) after the root post (4) has been inserted into a hole in said root, the majority of the fibers (5) that reinforce the post (4) are more than 3 mm long, characterized in that:

the connection between the crown reconstruction base (1) and the post (4) is achieved by polymerization of the material of said base under an isostatic charge, after placing an auxiliary forming part (7) on the upper part of the base, and the fibers (5) that reinforce the post (4) have a different direction from that of the longitudinal axis of the post (4), so as to adjust the post's modulus of elasticity close to that of the natural dentine, independently from the angle of incidence of the force applied to the tooth, with an assembly tensile strength greater than 200 MPa.

2. Crown-and-root reconstruction assembly according to claim 1, characterized in that the fibers (5) that reinforce the post (4) are arranged in a helical structure with predetermined diameter and threading and/or rate of fibers along the crown portion to the root portion of the post (4).

3. Crown-and-root reconstruction assembly according to claim 1, characterized in that the fibers (5) that reinforce the post (4) are subject to a predetermined crossing or weaving.

4. Crown-and-root reconstruction assembly according to claim 1, characterized in that the fibers (5) that reinforce the post (4) have a three-dimensional organization, with the tooling axis (aa') of the post (4) at an angle ranging from 20° to 70° in relationship to each of the three axes (x,y,z).

5. Crown-and-root reconstruction assembly according to claim 1, characterized in that the fibers (5,2) that reinforce the post (4) and reconstruction base (1) are made from materials that act as light guides.

6. Crown-and-root reconstruction assembly according to claim 1, characterized in that after polymerization under isostatic pressure, the composite material that constitute the crown reconstruction base (1), comprises a quantitative ratio of approximately 75% fibers and 25% resin.

7. Crown-and-root reconstruction assembly according to claim 1, characterized in that a support shell (26) made out of composite material is glued in the lower side of a crown (25) that is the dental prosthesis, and the gluing process is achieved with a resin of the same nature as that of said shell (26) and the first matrix (3), and that the support shell (26) represents an intermediary transition layer that has a modulus of elasticity close to that of the natural dentine in order to help dampen shocks.

8. Forming process for a crown-and-root reconstruction assembly according to claim 1, characterized in that:

a preform is used as the paste for the crown reconstruction base (1) that is in a pasty state prior to polymerization, and that is included in a case or a syringe, isostatic pressure is exerted through an elastic and translucent membrane (22) that is distorted when an internal space (24) of the preform is placed in a vacuum, the preform being coated on the post (4) and an interface

(10) between the root and the face and is formed via a person's fingers through the membrane (22), and the polymerization is implemented by illumination of a light source.

9. Forming process for a crown-and-root reconstruction assembly according to claim 1, characterized in that the isostatic pressure during polymerization is achieved via an enclosure (13) equipped with a bladder (14) that can be inflated by means of injecting a liquid (15) at a predetermined temperature and pressure.

10. Forming process for a crown-and-root reconstruction assembly according to claim 1, wherein the auxiliary forming part is comprised of a light transparent material, the connection is polymerized by passing light through the auxiliary forming part, and the auxiliary forming part is disposed of after the photo-polymerization phase.

11. Forming process for a crown-and-root reconstruction assembly according to claim 10, wherein the auxiliary forming part further comprises a dummy opening positioning hole, the dummy opening positioning hole is used to locate the auxiliary forming part straight to said post, and said dummy opening positioning hole forms a piston cylinder and serves as a stop for the upper end of said post.

12. The forming process of claim 10, wherein the light source comprises an optical fiber.

* * * * *